United States Patent [19]

Lloyd et al.

[11] Patent Number: 5,177,005

[45] Date of Patent: Jan. 5, 1993

[54] METHOD FOR MAINTAINING IMMOBILIZED GLUCOSE ISOMERASE ACTIVITY DURING CONTINUOUS ISOMERIZATION OF GLUCOSE TO FRUCTOSE

[75] Inventors: Norman E. Lloyd; Richard L. Antrim, both of Sparta, N.J.

[73] Assignee: Stabra AG, Zug, Switzerland

[21] Appl. No.: 762,034

[22] Filed: Sep. 16, 1991

Related U.S. Application Data

[63] Continuation of Ser. No. 649,166, Feb. 1, 1991, abandoned, which is a continuation of Ser. No. 287,964, Dec. 21, 1988, abandoned, which is a continuation-in-part of Ser. No. 636,879, Aug. 2, 1984, abandoned.

[51] Int. Cl.$^5$ ............... C12P 19/24; C12N 11/12; C12N 11/08; C12N 9/92
[52] U.S. Cl. ............... 435/94; 435/179; 435/180; 435/234
[58] Field of Search ............... 435/94, 174, 177, 178, 435/179, 180, 234

[56] References Cited

U.S. PATENT DOCUMENTS

| | | | |
|---|---|---|---|
| 3,788,945 | 1/1974 | Thompson et al. | 435/94 |
| 3,909,354 | 9/1975 | Thompson et al. | 435/94 |
| 3,960,663 | 6/1976 | Tamura et al. | 435/94 |
| 4,110,164 | 8/1978 | Sutthoff et al. | 435/179 |
| 4,355,117 | 10/1982 | Antrim et al. | 521/28 |
| 4,411,996 | 10/1983 | Lloyd | 435/94 |

FOREIGN PATENT DOCUMENTS

| | | |
|---|---|---|
| 949909 | 6/1974 | Canada. |
| 1143308 | 3/1983 | Canada. |

OTHER PUBLICATIONS

Immobilized Enyzmes—Modern State & Prospects Edited by I. V. Berezin et al., vol. 1, 1974, pp. 133-135-In Russian.
Enzyme Activity Maintenance In Packed Bed Reactors Via Continuous Enzyme Addition; F. H. Verhoff et al.; Biotechnology & Bioengineering, vol. XXIII, pp. 41-60, 1981.

*Primary Examiner*—David M. Naff
*Attorney, Agent, or Firm*—Margaret A. Horn; James G. Passe

[57] ABSTRACT

This invention provides a method for the maintenance of continuous activity of an immobilized enzyme reaction by initially underloading an adsorbent with a desired enzyme, monitoring the activity of the enzyme and periodically adding fresh enzyme to maintain a constant, continuous level of activity until the maximum carrying capacity of the support is reached. The method is preferably carried out when continuously isomerizing glucose to fructose with glucose isomerase adsorbed to a weakly basic anion exchange resin.

6 Claims, No Drawings

METHOD FOR MAINTAINING IMMOBILIZED GLUCOSE ISOMERASE ACTIVITY DURING CONTINUOUS ISOMERIZATION OF GLUCOSE TO FRUCTOSE

CROSS REFERENCES TO RELATED PATENT APPLICATIONS

This patent application is a continuation of application Ser. No. 07/649,166, filed Feb. 1, 1991, now abandoned, which is a continuation of application Ser. No. 07/287,964, filed Dec. 21, 1988, now abandoned, which is a continuation-in-part of application Ser. No. 636,879 filed Aug. 2, 1984, now abandoned.

FIELD OF THE INVENTION

This invention relates to the field of immobilized enzyme technology. More specifically, the invention provides a method for maintaining a desired level of enzyme activity during a continuous conversion process.

BACKGROUND OF THE INVENTION

Although examples of protein immobilization may be found dating to the early 1920's (Nelson, J. M. and E. I. Hitchcocks, J. Amer. Chem. Soc. 46:1956 [1921]), intense interest in the phenomenon is evident from the last quarter of a century. Immobilization strategies can be grouped into four general classes: (1) entrapment (2) cross-linking (3) covalent binding and (4) adsorption.

Entrapment strategies are generally based upon occlusion within cross-linked gels or encapsulation with hollow fibers, liposomes, microcapsules and the like. Cross-linking involves modification of the enzyme by the addition of so-called bi-or multifunctional cross-linking reagents often following adsorption or encapsulation. Covalent-linking, the most widely investigated strategy, involves the covalent binding of the enzyme to a support by means of functional groups which are nonessential for the biological activity of the enzyme. Adsorption is achieved by simply contacting the enzyme with an adsorbent and allowing the immobilization to result from the interaction of the relatively weak binding forces between the enzyme and the adsorbent.

It is to this latter strategy of immobilization that this invention most directly relates; therefore, certain principles of adsorption will be developed more fully below. Comprehensive reviews of entrapment, cross-linking and covalent binding exist (See for example: Weetal, H. H., ed. "Immobilized Enzymes, Antigens, Antibodies and Peptides" M. Dekker, New York, [1975], or Zaborsky O. R. "Immobilized Enzymes" CRC Press, Cleveland, [1973]).

Early investigation concerning adsorption indicated that in certain cases the adsorption could lead to partial or total inactivation of the enzyme. It is therefore appreciated that a suitable adsorbent for the practice of this invention is one which possesses a relatively high affinity for the enzyme, yet causes minimal inactivation.

Adsorption immobilization to such supports as alumina, bentonite, calcium carbonate, cellulose, collagen, ion exchange resins, kalinite, Sephadex, silica gel and titanium-coated stainless steel is known.

Although, as disclosed below, this invention is adaptable to a wide range of adsorbed enzyme systems, it is particularly suited for the beneficiation of processes employing immobilized glucose isomerase.

Most fructose is commercially produced by isomerizing dextrose (from starch) to fructose in a reactor whereby dextrose solution is passed through a bed of immobilized glucose isomerase. The fructose content of effluent is typically held at a constant level. e.g., between 40–44%, by controlling the flow rate through the reactor. As the immobilized enzyme naturally decays due to thermal and chemical inactivation the flow rate is periodically reduced. When a flow rate is reached beyond which further reduction is impractical the immobilized enzyme is replaced with a new bed of immobilized enzyme. Because flow rate of a column during its lifetime may vary from, e.g., 50 GPM to 4 GPM, numerous columns must be in place to provide a nearly constant production rate.

Particularly useful systems for the immobilization of glucose isomerase have been described in U.S. Pat. Nos. 3,788,945, 3,909,354, 4,110,164, 4,168,250 and 4,355,117. U.S. Pat. No. 3,960,663 describes periodic addition of soluble glucose isomerase via the dextrose feed stream to an isomerization reactor containing immobilized glucose isomerase. The glucose isomerase is immobilized to a strong base anion-exchange resin which has been loaded to capacity with soluble glucose isomerase. As the enzyme decays, its adsorption properties are altered such that the inactive enzyme is sloughed off the support and appears in the eluent. The patent teaches to replace the leeched enzyme by contacting the support with fresh enzyme in an amount sufficient to totally re-charge the support. Since the spent enzyme is continually leeched from the adsorbent the eluent must be subjected to a further purification step in order to remove the contaminating enzyme.

The application of the subject invention leads to significant advantages over conventional reactions with respect to: (1) simplification of operations—the need to adjust reactor flows on a periodic bases would be eliminated; (2) lower capital investment—smaller reactors would be needed in favor of a few large reactors due to elimination of fluctuating flow rates; (3) improved production control—higher fructose levels could be achieved with no need for reduced flow rates by addition of more soluble enzyme to the reactor; and, (4) reduced product-refining costs—because very slow flow rates and hence long residence times would be eliminated, production of color and off-flavors would be lessened.

BRIEF DESCRIPTION OF THE INVENTION

This invention provides a method for maintaining constant activity of an immobilized enzyme reactor comprising adsorbing to a solid support under adsorbing conditions an amount of enzyme representing a predetermined level of activity and less than the maximum carrying capacity of said support, optionally monitoring the enzyme activity and adsorbing additional amounts of enzyme to said support to maintain said predetermined level of activity of the previously adsorbed enzyme. The addition of enzyme is continued until the maximum carrying capacity of the support is reached. The invention is particularly useful for maintaining the activity of an immobilized glucose isomerase reaction such as may be used in the production of fructose from glucose.

DETAILED DESCRIPTION OF THE INVENTION

A major factor in determining the effectiveness of an immobilized enzyme process is the length of time the enzyme charge remains active. As mentioned above, the enzyme naturally decays as the process proceeds. Although not wishing to be bound by a particular theory of how the enzymes decay, it is believed that thermal as well as chemical denaturation are contributors to the decay.

One response to this problem has been simply to reduce the flow of reactants through the immobilized system as the efficiency of the system drops. However, since flow rates can vary by a factor of 10 or more, it is necessary to establish a series of columns in order to provide for a continuous output. Other responses have been to suspend operations of the system periodically, remove the spent enzyme and recharge with fresh enzyme; or as described in U.S. Pat. No. 3,960,663, add fresh enzyme periodically as the spent enzyme is leeched into the eluent.

The invention provides an approach which is superior to those discussed above in that fresh enzyme may be added to the system without suspending operation, the output can be maintained at a constant level or, if desired, can be increased and the eluent is substantially free of spent enzyme.

This invention provides a method wherein during the initial preparation of an immobilized system the enzyme is added to the support in an amount which is less than the maximum carrying capacity of the adsorbent, i.e., the support is underloaded, thus a constant output is maintained by introducing fresh enzyme as necessary until such time as the maximum carrying capacity of the support is reached.

Since adsorption based immobilization techniques reflect the charge interactions of the enzyme with the support, hydrophobic interactions between enzyme and support, etc., the choice of a particular enzyme-support combinations must be determined empirically. Useful supports include:

1. Weak base polystyrene resins such as: Amberlite IRA-93 (Rohm & Haas), Diaion WA-30 (Mitsubishi), Diaion WA-11 (Mitsubishi), Amberlite IR-45 (Rohm & Haas);

2. Weak base (-N(R)$_2$)phenol-formaldehyde resins such as: Duolite EA-561 (Diamond Shamrock), Duolite ES-562 (Diamond Shamrock), Duolite ES-568 (Diamond Shamrock);

3. Strong base (-N(R)$_3$)polystyrene resins such as: XE-352 (Rohm & Haas), Amberlite IRA-900 (Rohm & Haas), Amberlite IRA-904 (Rohm & Haas), Amberlite IRA-938 (Rohm & Haas), GIA-01 (Mitsubishi), Diaion PA-308 (Mitsubishi), Diaion PA-304 (Mitsubishi), Diaion SA-21A (Mitsubishi), Sumitomo Resin (Sumitomo Co. Ltd., Japan);

4. Miscellaneous Enzyme Adsorbants such as: DEAE-Sephadex (Derivatized crosslinked dextran—Pharmacia), DEAE-Glycophase (Controlled pore glass coated with carbohydrate and derivatized—Pierce Chemical Co.), QAE-Glycophase (Strong base counterpoint to above), DEAE-Biogel A (Derivatized crosslinked agarose gel beads—Bio-Rad), Selectacel DEAE-cellulose Granular. Brown Co., Vistec D2 & D3 (Granular DEAE-cellulose from viscose—Viscose Group Ltd.), DEAE Sephacel (Bead DEAE-cellulose—Pharmacia), DEAE-Cellulose Beads (U.S. Pat. No. 4,090,022), DEAE-Cellulose Beads (Polytechna, Czechoslovakia), Controlled Pore Glass (Corning Glass) and Controlled Pore Aluminia, Titania, Zirconia (Corning Glass).

It is preferred to use those supports which are weakly basic anion exchange supports. Most preferred being DEAE Sephadex or DEAE-Cellulose type supports.

The preferred supports also have a capacity for the enzyme adsorbed thereon of at least about 684 IGIU/gram of support, or at least about 222 IGIU/ml of support, on a dry basis.

A wide variety of enzymes may be adsorbed to the above supports; the particular support may be easily selected by the skilled artisan without undue experimentation. It is preferred to employ such enzymes as glucose isomerase, glucoamylase, aminoacylase, invertase, $\beta$-glucanase, glucose-1-oxidase and glucose-2-oxidase.

If the immobilization is based solely on electrostatic attraction there is a possibility for the conjugates to dissociate when the ionic strength, pH, or temperature of the reaction is varied. It is preferred to select an enzyme which binds with high avidity to the support to minimize these effects. Alternatively, it is possible to increase the charge on the protein by chemical modification, such as was done with amyloglucosidase by Solomon and Levine (Biotechn. Bioeng. 16:1161[1974]). A particularly useful enzyme for practicing the subject invention is glucose isomerase.

Although not intended to limit the scope of the invention, the following Examples provide specific details relative to one particular enzyme/support combination.

EXAMPLE 1

This example describes periodic addition of a partially purified, soluble glucose isomerase to an isomerization reactor containing a partially loaded carrier in a manner such that essentially a constant rate of isomerization was maintained for 8 weeks. The activity was thereafter doubled and maintained at the elevated level for an additional 19 weeks.

PURIFICATION OF SOLUBLE ENZYME

A 1460 ml batch of *Streptomyces rubiginosus* fermentation broth was filtered, and the cells were resuspended in 730 ml deionized water and refiltered twice. The cells were reslurried in 1460 ml of deionized water. The pH of the slurry was adjusted to 6.5 with dilute HCl, and 10 mg of lysozyme and 1700 ppm Variquat (a dimethylalkylbenzylammonium chloride) were added. The mixture was incubated at 40° C. for 3.6 hours with gentle overhead stirring to extract soluble isomerase from the cells. The soluble enzyme was removed from cellular debris by filtration and assayed at 18 IGIU/ml. See Lloyd, N. E., Khaleeluddin, K. and Lamm, W. R. (1972), Cereal Chem. 49, 544 for a description of the assay method. The International Glucose Isomerase Unit is defined as that amount of enzyme which catalyzes the transformation of D-glucose to D-fructionse at the rate of 1 $\mu$mole/minute under the specified conditions (pH 7.0, 60° C., 2.0M glucose, 0.02M Mg++, 0.001M Co++, 0.2M sodium maleate buffer).

CARRIER FOR IMMOBILIZATION

The weak-base carrier used to immobilize soluble glucose isomerase was a granular DEAE-cellulose (GDC). The general method of preparation whereby ground cellulose and a weighting agent are agglomerated with plastic and then the cellulose is derivatized with diethylaminoethyl chloride to impart weak base properties thereto is described in U.S. Pat. No. 4,355,117 assigned to Nabisco Brands, Inc.

Specifically a mixture of 36 lb. C-100 ground cellulose (International Filler Corp.) and 24 lb. calcined alumina (Reynolds RC-20) was compounded with 60 lbs. of high-impact polystyrene (Hammond Plastics) on a 200° C. roll mill until the plastic was molten and the mixture was homogeneous. The granular cellulose composite was cooled, ground by multiple passes through a hammer mill and screened to yield a 40 to 80 U.S. Standard mesh fraction. The screened material (36 lbs.) was slurried in an alkaline sulfate solution comprised of 37 lbs. sodium sulfate, 4.8 lbs. sodium hydroxide and 14.1 gallons water. The slurry was heated to 40° C. and 14.15 lb. of a 50% water solution of diethylaminoethyl chloride hydrochloride was metered into the slurry with stirring at a rate of 115 ml/minute (about 1 hour addition time). The slurry was stirred an additional 30 minutes, 7.2 lbs. of 50% NaOH was added and another 14.15 lbs. of 50% diethylaminoethyl chloride hydrochloride was metered in as above. The slurry was heated to 60° C., diluted with 15 gallons water, pH adjusted to 4.5 with HCl and washed over a 60 mesh shaker screen. The GDC was reslurried, pH adjusted to 7.0-7.5 and dewatered on a 60 mesh screen.

The adsorption capacity of the carrier was measured as follows. To 100 ml soluble enzyme was added 2.63 g dry basis carrier. The pH was adjusted to 7.0 and the slurry was agitated gently for 5 hours. Adsorption was followed by filtering aliquots at timed intervals and measuring soluble isomerase activity.

| Time Hours | Soluble Activity IGIU/ml | % Adsorbed |
| --- | --- | --- |
| 0 | 18.0 | 0 |
| .25 | 12.7 | 29.4 |
| 1 | 5.8 | 67.8 |
| 2 | 2.5 | 86.1 |
| 3 | 1.2 | 93.3 |
| 4 | 0.4 | 97.8 |
| 5 | 0 | 100 |

The measured capacity of the carrier for soluble isomerase was therefore about 684 IGIU/g dry basis.

INITIAL ENZYME IMMOBILIZATION OF GDC

GDC carrier was partially loaded with soluble isomerase to about 25% of capacity as follows. GDC (14.8 g dry basis) was slurried in deionized water and the pH adjusted to 7.0-7.1. The slurry was deaerated under water-aspirator vacuum at room temperature for 60 minutes and was poured into a one inch diameter by 12 inch long Ace Glass Ajustachrom ® jacketed glass column fitted with a fritted glass bottom. The bed was packed to a depth of 3.54 inches. Glass beads were placed on top of the bed (4 inches) to distribute flow. The GDC was loaded by pumping 145 ml (2600 IGIU) of soluble isomerase downflow through the bed at 1 ml/minute and room temperature. No measurable soluble activity passed through the bed.

Since the column has a one inch diameter and the bed of partially loaded carrier therein was packed to a depth of 3.54 inches, the volume of the bed in the column was 45.56 ml or cm³, based on the equation $$\text{column volume} = (0.5 \text{ inches})^2 (\pi) (3.54 \text{ inches}) (2.54)^{3*}$$
$$= 45.54 \text{ ml (or cm}^3)$$

Then since the column contained 14.8 grams of the carrier, and the enzyme capacity of the carrier was 684 IGIU/gram of carrier, the capacity of the carrier in the column was 222 IGIU/ml of carrier, based on the equation $$\text{carrier capacity} = \frac{684 \times 14.8}{45.56} = 222 \text{ IGIU/ml}.$$

Thus the carrier had a capacity of at least 222 IGIU/ml or 684 IGIU/gram on a dry basis.

ASSAY OF IMMOBILIZED ISOMERASE ACTIVITY

The water jacket on the column was attemperated at 61° C. A 50% solution of crystalline dextrose at pH 7.8 containing 5 mM MgSO$_4$ and 5 mM NaHSO$_3$ was started downflow through the bed of immobilized isomerase at a flow rate of 0.4 ml/minute. The column was run 16 hours. A sample of effluent was taken for analysis and the immobilized activity was determined according to the following equation:

$$E_t = \frac{RC}{k_f} \ln \left[ \frac{I_e - I_o}{I_e - I} \right] \tag{1}$$

where
$E_t$ = total immobilized activity in IGIU
$R$ = flow rate in ml/hour
$C$ = monosaccharide concentration in g/ml
$k_f$ = reaction rate constant at 61° C. (0.019 g/IGIU/hour)

$I$ = degree of isomerization of effluent
$= \frac{\text{fructose concentration}}{\text{monosaccharide concentration}}$ $I_o = I$ of influent = 0 for crystalline dextrose
$I_e = I$ at equilibrium = 0.510 at 61° C.

Degree of isomerization, I, was measured polarimetrically as follows: Samples of column influent and effluent were diluted 20 fold with deionized water and held 1 hour to allow rotation equilibrium to be reached. Rotation measurements were made on a Perkin Elmer Model 241 polarimeter at 25° C. with a mercury source wavelength of 576 nm. The instrument was zeroed with water in the cell and rotation readings in degrees of the diluted influent and effluent were taken.

$$I = \left( \frac{\text{influent rotation} - \text{effluent rotation}}{\text{g monosaccharide/ml diluted influent or effluent}} \right) \times \text{Factor} \tag{2}$$

where $I = I_o$ $$\text{Factor} = \frac{D}{L([\alpha_d] - [\alpha_f])}$$

D = dilution factor (5 ml-100 ml) = 20

L = polarimeter cell length = 1 dm $[\alpha_d] - [\alpha_f]$ = change in specific rotation for converting pure dextrose to pure fructose : measured with mercury light = 167.33.

Factor = 0.1195

The immobilized activity determined by the assay method was 1548 IGIU indicating that of the 2600 IGIU soluble activity loaded on the carrier, 60% was expressed as immobilized activity.

ISOMERIZATION AND PERIODIC ENZYME ADDITION

A 50% solution of cornstarch hydrolyzate containing dextrose on a dry solids basis, 5 mM MgSo₄ and 5 mM NaHSO₃ was adjusted in pH to 7.8, and started downflow through the bed of immobilized isomerase at 61° C. Initial flow through the column was calculated from equation 1 and was set to provide a fructose conversion of about 44%. This flow of about 17 ml/hour was held constant except during assay of immobilized activity. Fructose content of the effluent was measured essentially by the method as for determining degree of isomerization.

$$\% \text{ fructose} = 100 \, I_d$$

where d = monosaccharide content of effluent expressed as fraction of total dry solids.

Fructose level dropped gradually over a period of 16 days to about 40% whereupon the first addition of soluble enzyme was made. An assay of immobilized activity indicated that about 800 IGIU was required to replenish lost activity and increase fructose conversion to 44%. Accordingly, 40 ml of enzyme (720 IGIU) was added to 126 ml of 50% crystalline dextrose solution containing salts as above. Feed to the column was switched to the enzyme-containing dextrose solution and was allowed to flow at 0.3 ml/minute until depletion. Effluent taken from the column during the enzyme-adsorption process was found to contain no soluble isomerase (determined by incubating effluent 16 hours at 61° C. and measuring for increased fructose content). Crystalline dextrose solution was then continued as feed to assay the additional immobilized activity. Feed was switched back to cornstarch hydrolysate and the effluent fructose level was restored to 44%.

This sequence of allowing the fructose level in the effluent to gradually decrease to about 40%, switching to a crystalline dextrose feed solution for assay of immobilized activity, addition of soluble enzyme through the dextrose feed stream, reassay for added immobilized activity and switching back to cornstarch hydrolyzate feed was continued for 17 weeks. For the remaining 10 weeks of the trial, the sequence was modified to eliminate assay of immobilized activity before and after enzyme addition. A constant amount of soluble enzyme was periodically added thereafter. Fructose during this time was allowed to vary only between the arbitrarily set limits of 40–44% with flow rate being held constant. Of course, tighter limits could be set necessitating more frequent additions of soluble enzyme.

After 7.5 weeks of operation enzyme activity in the column was double with no significant effect on the operations other than allowing a faster flow rate to achieve 40%–44% fructose. After 13 weeks of operation, the level of salts in the cornstarch hydrolyzate feed were dropped to 1 mM MgSO₄ (from 5 mM) and 2 mM NaHS)₃ (from 5 mM).

At 20 weeks assay of effluent taken during enzyme loading indicated some leakage of soluble activity. The last enzyme addition made before leakage occurred brought the total enzyme adsorbed to a value of 649 IGIU/g or close to the capacity measured initially of 684 IGIU/g. Leakage increased during subsequent loading operations although sufficient fresh enzyme was adsorbed to maintain fructose conversion of over 40%. The fact that enzyme was still adsorbed after the initially measured capacity had been exceeded indicated that some inactive enzyme may be desorbed.

Table I summarizes fructose production and enzyme additions over the 27 week trial. The amount of fructose produced is expressed as grams of 43% fructose syrup on a dry basis. Weekly actual fructose production data was normalized to 43% fructose production.

TABLE I

SUMMARY OF ISOMERIZATION AND ENZYME ADDITION

| Week | Enzyme Addition IGIU | Enzyme Accumulation IGIU | Average Fructose % | Accumulative Fructose g 43% dry basis | Enzyme Efficiency IGIU/g of 43% F |
|---|---|---|---|---|---|
| 1 | 2600 | 2600 | 43.7 | 2059 | 1.26 |
| 2 | | | 42.5 | 3606 | 0.72 |
| 3 | 720 | 3320 | 39.1 | 4851 | 0.68 |
| 4 | | | 42.3 | 6533 | 0.51 |
| 5 | | | 43.1 | 8292 | 0.40 |
| 6 | | | 41.6 | 9891 | 0.34 |
| 7 | | | 39.8 | 11298 | 0.29 |
| 8 | 3200 | 6520 | 39.5 | 12379 | 0.53 |
| 9 | | | 44.7 | 15293 | 0.43 |
| 10 | | | 44.6 | 18302 | 0.36 |
| 11 | | | 43.5 | 20476 | 0.32 |
| 12 | | | 43.6 | 22789 | 0.29 |
| 13 | 470 | 6990 | 41.1 | 24856 | 0.28 |
| 14 | 940 | 7930 | 41.4 | 26764 | 0.30 |
| 15 | | | 44.3 | 29322 | 0.27 |
| 16 | | | 40.4 | 31298 | 0.25 |
| 17 | 940 | 8670 | 43.4 | 33733 | 0.26 |
| 18 | | | 40.7 | 35433 | 0.24 |
| 19 | 940 | 9610 | 43.2 | 37949 | 0.25 |
| 20 | 940 | 10550 | 42.7 | 40162 | 0.26 |
| 21 | | | 42.0 | 42264 | 0.25 |
| 22 | 940 | 11490 | 43.3 | 44497 | 0.26 |
| 23 | | | 41.9 | 46730 | 0.25 |
| 24 | 940 | 12430 | 41.9 | 48811 | 0.25 |
| 25 | | | 44.5 | 51011 | 0.24 |
| 26 | | | 43.0 | 52737 | 0.24 |
| 27 | 770 | 13200 | 41.1 | 54528 | 0.24 |

EXAMPLE II

This example described on-column loading whereby the soluble glucose isomerase used to partially load the carrier initially and for subsequent additions is of high purity. Column operations were the same as for Example I in that the flow rate of cornstarch-hydrolyzate feed was held constant and periodic additions of soluble enzyme in a solution of crystalline dextrose were made through the feed line. Fructose conversion was thus maintained between 40–44% for 14 weeks. The 45% solids refined cornstarch hydrolyzate feed contained about 95% dextrose, 1.5 mM MgSO₄, and 2.0 mM NaHSO₃. The pH of the influent was controlled around pH 7.8 to provide an effluent pH of 7.5; temperature of the immobilized enzyme bed was controlled at 60° C.

PURIFICATION OF SOLUBLE GLUCOSE ISOMERASE

*Streptomyces rubiginosus* fermentation broth was extracted to release soluble glucose isomerase from the cells as in Example 1 except that the cells were not separated from the broth and washed before extraction. A 2350 ml portion of the filtered extract was purified by fractionation on a granular DEAE-cellulose column. The granular DEAE-cellulose column was the same material as the carrier for immobilized enzyme in Example 1. To prepare the column 300 g dry basis GDC was equilibrated in 10 mM Tris buffer and the suspension poured into a 2 inch chromatography column to form a uniform bed. The column was washed with 2 liters of 10 mM Tris buffer at a flow of 10 ml/minute or until the effluent pH was about 7.

The enzyme solution containing 29.3 IGIU/ml was applied to the column downflow at a flow of 5 ml/minute. After the enzyme had been applied, the column was washed with 3.5 liters of 0.1M NaCl in 10 mM Tris buffer pH 7 at a flow of 10 ml/minute. Enzyme content of effluent fractions was monitored by ultraviolet absorbance and enzyme assay. Fractions containing greater than 20 IGIU/ml were pooled (900 ml) for additional purification by ultrafiltration. The pooled fractions were ultrafiltered with Amicon XM-100 membrane in an Amicon 407 stirred cell under 10 PSIG $N_2$. The ultrafilter retentate contained 800 IGIU/ml of about 50% pure enzyme.

CARRIER FOR IMMOBILIZATION

GDC carrier (7.75 g dry basis) was added to a glass column as described in Example 1. The carrier was loaded with purified enzyme to about 25% of its capacity by pumping downflow a 50% crystalline dextrose solution (pH 7.8, 4 mM $MgSO_4$, 5 mM $NaHSO_3$) containing 136 ml of the purified enzyme diluted 1 to 40 (2720 IGIU) at a flow rate of 0.4–0.7 ml/minute. No soluble enzyme was detected in the effluent. Flow of crystalline dextrose solution (pH 7.8, 5 mM $MgSO_4$, 5 mM $NaHSO_3$) was continued for assay and the column jacket attemperated with water such that the temperature of the column bed was 60° C.

ASSAY OF IMMOBILIZED ACTIVITY

Immobilized activity determined by the assay method of Example 1 was 1686 IGIU for an expression of activity based upon that adsorbed of 62%.

ISOMERIZATION AND PERIODIC ENZYME ADDITION

Cornstarch hydrolyzate was started through the bed of immobilized enzyme and the flow was adjusted to provide a fructose conversion of 40–44%. The flow rate was held constant at about 0.35 ml/minute for the duration of the trial. As the fructose level dropped with time due to enzyme decay, about a 20 ml aliquot of diluted, purified soluble isomerase containing 434 IGIU was added to a 50% solution of crystalline dextrose (pH 7.8, 5 mM $MgSO_4$, 5 mM $NaHSO_3$) and the solution pumped through the bed at about 0.4 ml/minute. After adsorption the feed was switched back to cornstarch hydrolyzate. Table II summarizes isomerization performance and enzyme additions. As in Example 1, essentially constant fructose conversion was maintained at a constant flow rate by means of periodic addition of soluble isomerase.

TABLE II
SUMMARY OF ISOMERIZATION AND ENZYME ADDITION

| Week | Enzyme Addition IGIU | Enzyme Accumulation IGIU | Average Fructose % | Accumulative Fructose g 43% dry basis | Enzyme Efficiency IGIU/g of 43% F |
|---|---|---|---|---|---|
| 1 | 2720 | 2720 | 33.5 | 1608 | 1.69 |
| 2 | 434 | 3154 | 41.3 | 3149 | 1.00 |
| 3 | 434 | 3588 | 42.9 | 4756 | 0.75 |
| 4 |  | 3588 | 43.6 | 6117 | 0.59 |
| 5 | 434 | 4022 | 42.3 | 8236 | 0.49 |
| 6 |  | 4022 | 43.1 | 9664 | 0.42 |
| 7 | 434 | 4456 | 41.6 | 11240 | 0.40 |
| 8 | 434 | 4890 | 41.0 | 12924 | 0.38 |
| 9 |  | 4890 | 41.9 | 14585 | 0.34 |
| 10 | 434 | 5324 | 45.1 | 16366 | 0.33 |
| 11 |  | 5324 | 43.2 | 18152 | 0.29 |
| 12 | 434 | 5758 | 42.1 | 19535 | 0.29 |
| 13 |  | 5758 | 42.4 | 21108 | 0.27 |
| 14 |  | 5758 | 38.7 | 22624 | 0.25 |

What is claimed is:

1. A continuous method for the isomerization of an influent of glucose to fructose with glucose isomerase comprising:
    a) adsorbing to a solid weakly basic anion exchange resin support, having a maximum capacity to bind glucose isomerase thereon of at least about 684 IGIU/gram, an amount of glucose isomerase which is about 10 to about 50% of the maximum capacity of the resin such that when exposed to an initial influent of a solution of glucose it will produce an initial effluent of about 40% to about 44% fructose that is free from glucose isomerase;
    b) subjecting the adsorbed glucose isomerase to an influent of a solution glucose such that the initial effluent is about 40% to about 44% fructose;
    c) adding glucose isomerase to the influent such the effluent is maintained about 40% to about 44% fructose and is free of glucose isomerase; and
    d) maintaining the influent of glucose and glucose isomerase until the effluent from the resin support is no longer free from glucose isomerase.

2. A method according to claim 1 wherein the amount of glucose isomerase absorbed if from about is from about 25% to about 50%.

3. A method according to claim 1 wherein the influent is maintained at about 60° C.

4. A method according to claim 1 wherein the resin selected is DEAE sephadex or DEAE cellulose.

5. A method according to claim 1 wherein glucose isomerase is added periodically.

6. A method according to claim 1 wherein glucose isomerase is added continuously.

* * * * *